United States Patent
Minami et al.

(10) Patent No.: US 7,943,370 B2
(45) Date of Patent: May 17, 2011

(54) STRUCTURE, TARGET SUBSTANCE DETECTION ELEMENT AND TARGET SUBSTANCE DETECTION KIT

(75) Inventors: Masato Minami, Yokohama (JP); Kazuhiro Ban, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 324 days.

(21) Appl. No.: 12/188,166

(22) Filed: Aug. 7, 2008

(65) Prior Publication Data
US 2009/0061533 A1 Mar. 5, 2009

(30) Foreign Application Priority Data
Aug. 23, 2007 (JP) .................. 2007-217580

(51) Int. Cl.
*C12M 1/34* (2006.01)
*C07C 303/00* (2006.01)
*C07C 309/04* (2006.01)
*A61K 31/205* (2006.01)

(52) U.S. Cl. ........ 435/287.2; 558/49; 562/109; 562/125

(58) Field of Classification Search ........................ None
See application file for complete search history.

(56) References Cited

U.S. PATENT DOCUMENTS

| | | |
|---|---|---|
| 2007/0105087 A1 | 5/2007 | Ban et al. |
| 2008/0090267 A1 | 4/2008 | Komatsu et al. |
| 2008/0108132 A1 | 5/2008 | Ban et al. |
| 2008/0278706 A1 | 11/2008 | Murayama et al. |
| 2008/0290268 A1 | 11/2008 | Komatsu et al. |

(Continued)

OTHER PUBLICATIONS

Frederix et al. Reduce nonspecific adsorption on covalently immobilized protein surfaces using poly(ethylene oxide) containing blocking agents. J. Biochem. Biophys. Methods 2004, vol. 58, pp. 67-74.*

(Continued)

*Primary Examiner* — Shafiqul Haq
(74) *Attorney, Agent, or Firm* — Fitzpatrick, Cella, Harper & Scinto

(57) ABSTRACT

A target substance detection element that can effectively prevent the nonspecific adsorption of a target substance or impurities and detects the target substance with high sensitivity, a target substance detection kit, and a structure constituting the target substance detection element. The structure has a substrate, polymers present on the substrate surface, and first target substance capturing molecules bonded to the polymers. The polymer is composed of a polymer of a carboxybetaine monomer represented by General Formula (1) below. The first target substance capturing molecules are bonded to some of the carboxyl groups of the polymers. A compound represented by General Formula (2) is bonded to at least some of the carboxyl groups, from among the carboxyl groups of the polymers, that are not bonded to the first target substance capturing molecules.

12 Claims, 5 Drawing Sheets

U.S. PATENT DOCUMENTS

2009/0000360 A1   1/2009   Ogawa et al.
2009/0005495 A1   1/2009   Ban et al.
2010/0099160 A1*  4/2010   Jiang et al. .................. 435/180

OTHER PUBLICATIONS

Lin et al. Development and application of side-pilished fiber immunosensor based on surface plasmon resonance for the detection of Legionella pneumophila with halogens light and 850nm-LED. Sensors and Actuators A 2007, vol. 138, pp. 299-306.*

Iwata, et al., "Control of Nanobiointerfaces Generated from Well-Defined Biomimetic Polymer Brushes for Protein and Cell Manipulations", Biomacromolecules, vol. 5, 2004, pp. 2308-2314.

Zhang, et al., "Dual-Functional Biomimetic Materials: Nonfouling Poly(carboxybetaine) with Active Functional Groups for Protein Immobilization", Biomacromolecules, 2006, vol. 7, pp. 3311-3315.

U.S. Appl. No. 11/995,911, filed Jan. 16, 2008, Imamura, et al.

U.S. Appl. No. 12/065,720, filed Mar. 4, 2008, Ban, et al.

* cited by examiner

STRUCTURE, TARGET SUBSTANCE DETECTION ELEMENT AND TARGET SUBSTANCE DETECTION KIT

BACKGROUND OF THE INVENTION

1. Field of the Invention

The present invention relates to a target substance detection element that can effectively prevent the nonspecific adsorption of a target substance or impurities and detects the target substance with high sensitivity, a target substance detection kit, and a structure constituting the target substance detection element.

2. Description of the Related Art

Intermolecular interaction has been employed for a long time as means for detecting a target substance in an analyte. A method by which molecules of one type are immobilized as capturing molecules onto a substrate surface and a reaction is induced by bringing an analyte containing a target substance into contact therewith is a typical method using such interaction.

When a target substance that interacts with the immobilized capturing molecule is quantitatively measured, with certain materials of substrate surface or immobilization methods, substances that have been nonspecifically adsorbed on the substrate surface in addition to the target substance that has interacted with the biomolecules can be also detected at the same time. This can decrease minimum detection sensitivity in sensors requiring microdetection. Therefore, a method for detecting only the target substance, while inhibiting the nonspecific adsorption, is required.

A method by which an MPC (2-methacryloyloxyethyl phosphorylcholine) polymer is formed at a high density on a silicon substrate surface by atom transfer radical polymerization using MPC as a monomer and the nonspecific adsorption of proteins and adhesion of cells are prevented has been disclosed as a technique for preventing nonspecific adsorption on a substrate surface in "Biomacromolecules", 2004, 5, pp. 2308 to 2314 (Non-patent Document 1).

However, the MPC polymer used in the above-described non-patent document 1 is not a structure that can immobilize the target substance capturing molecules and the immobilization has not been performed.

On the other hand, "Biomacromolecules", 2006, 7, pp. 3311 through 3315 (Non-patent Document 2) discloses a method by which a CBMA (carboxybetaine methacrylate) polymer is formed at a high density on an SPR (Surface Plasmon Resonance) sensor surface by atom transfer radical polymerization using CBMA as a monomer, and then target substance capturing molecules are immobilized onto carboxyl groups that are side-chain functional groups of the CBMA polymer, the nonspecific adsorption of impurities is prevented, and the target substance is detected.

In the above described non-patent document 2, active ester groups (succinimide groups) are deactivated by ethanolamine after the target substance capturing molecules have been immobilized on the CBMA polymer. Therefore, the negative electric charge of the carboxyl groups of the side-chain betaine structure disappears and the electric charge of the side chain shifts from neutral to positive. As a result, the nonspecific adsorption of impurities bearing a negative electric charge can occur and functionality of the immobilized target substance capturing molecules can further deteriorate.

SUMMARY OF THE INVENTION

In accordance with the present invention, it is possible to provide a target substance detection element that can effectively prevent the nonspecific adsorption of a target substance or impurities and detect the target substance with high sensitivity, a target substance detection kit, and a structure constituting the target substance detection element.

The first aspect of the present invention resides in a structure having a substrate, polymers present on a surface of the substrate, and first target substance capturing molecules bonded to the polymers, wherein the polymer comprises a polymer of a carboxybetaine monomer represented by General Formula (1) below;

the first target substance capturing molecules are bonded to some of the carboxyl groups of the polymers; and a compound represented by General Formula (2) is bonded to at least some of the carboxyl groups, from among the carboxyl groups of the polymers, that are not bonded to the first target substance capturing molecules.

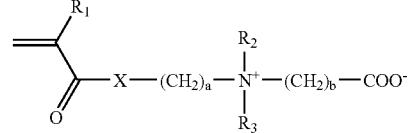

(1)

(in this formula, $R_1$ is a hydrogen atom or a methyl group; $R_2$ and $R_3$ are independently selected from a methyl group, an ethyl group, an n-propyl group, and an iso-propyl group; X is an oxygen atom or NH; a is an integer from 1 to 5; b is an integer equal to or larger than 1 and equal to or smaller than 4).

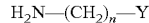

(2)

(in this formula, n is integer equal to or larger than 1 and equal to or smaller than 4, such that n+b is an integer from 2 to 5; Y is any group from among —COOH, —OSO$_3$H, —SO$_3$H, —OPO(OH)(OR$_7$), —PO(OH)(OR$_8$) (R$_7$ and R$_8$ are each independently a methyl group or an ethyl group); the hydrogen atom of the methylene group may be substituted with a hydroxyl group, a methyl group, or a hydroxymethyl group).

The compound represented by the General Formula (2) is preferably any from glycine, β-alanine, aminomethanesulfonic acid, and monoaminoethyl sulfate.

The compound represented by the General Formula (1) is preferably a compound represented by General Formula (3) below.

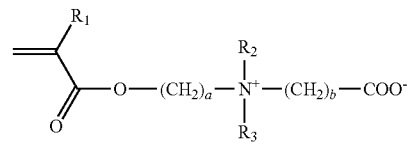

(3)

(in this formula, $R_1$ is a hydrogen atom or a methyl group; $R_2$ and $R_3$ are independently selected from a methyl group, an ethyl group, an n-propyl group, and an iso-propyl group; a is an integer from 1 to 5; b is an integer equal to or larger than 1 and equal to or smaller than 4).

The compound represented by the General Formula (1) is preferably a compound described by the following Chemical Formula (A), and the compound described by the General Formula (2) is preferably any from glycine, β-alanine, aminomethanesulfonic acid, and monoaminoethyl sulfate.

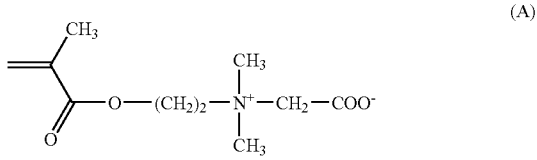

(A)

Another aspect of the present invention resides in a target substance detection element having a substrate having a detection region, polymers present on a surface of the substrate, and first target substance capturing molecules bonded to the polymers, wherein the polymer comprises a polymer of a carboxybetaine monomer represented by General Formula (1) below;

the first target substance capturing molecules are bonded to some of the carboxyl groups of the polymers; and a compound represented by General Formula (2) is bonded to at least some of the carboxyl groups, from among the carboxyl groups of the polymers, that are not bonded to the first target substance capturing molecules.

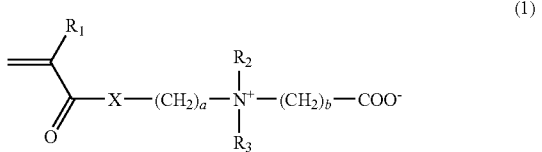

(1)

(in this formula, $R_1$ is a hydrogen atom or a methyl group; $R_2$ and $R_3$ are independently selected from a methyl group, an ethyl group, an n-propyl group, and an iso-propyl group; X is an oxygen atom or NH; a is an integer from 1 to 5; b is an integer equal to or larger than 1 and equal to or smaller than 4).

$$H_2N-(CH_2)_n-Y \quad (2)$$

(in this formula, n is integer equal to or larger than 1 and equal to or smaller that 4, such that n+b is an integer from 2 to 5; Y is any group from among —COOH, —$OSO_3H$, —$SO_3H$, —OPO(OH)($OR_7$), —PO(OH)($OR_8$) ($R_7$ and $R_8$ are each independently a methyl group or an ethyl group); the hydrogen atom of the methylene group may be substituted with a hydroxyl group, a methyl group, or a hydroxymethyl group).

Yet another aspect of the present invention resides in a target substance detection kit comprising the above-described target substance detection element and a labeling material comprising a labeling substance and a second target substance capturing molecule.

Further, the detection region is preferably a region that can detect a magnetic substance, and the labeling substance is preferably a magnetic substance.

Further features of the present invention will become apparent from the following description of exemplary embodiments (with reference to the attached drawings).

DESCRIPTION OF THE EMBODIMENTS

The structure according to the first aspect of the present invention will be described below with reference to FIGS. 1A and 1B.

Figure 1A:
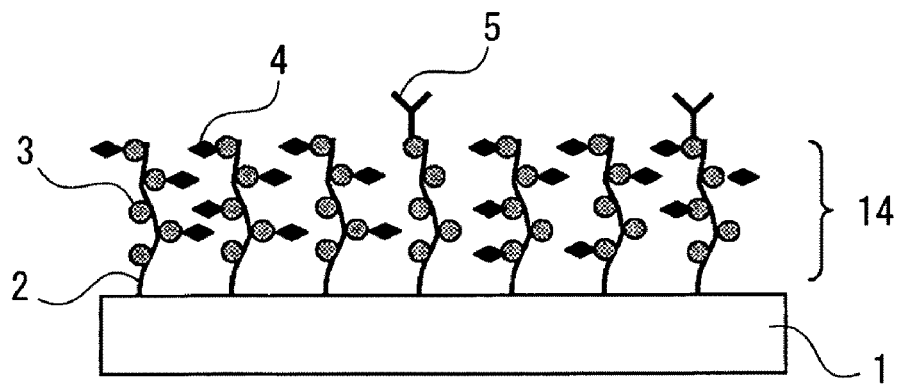
FIGS. 1A and 1B are schematic drawings illustrating an example of the structure in accordance with the present invention.
Figure 1B:
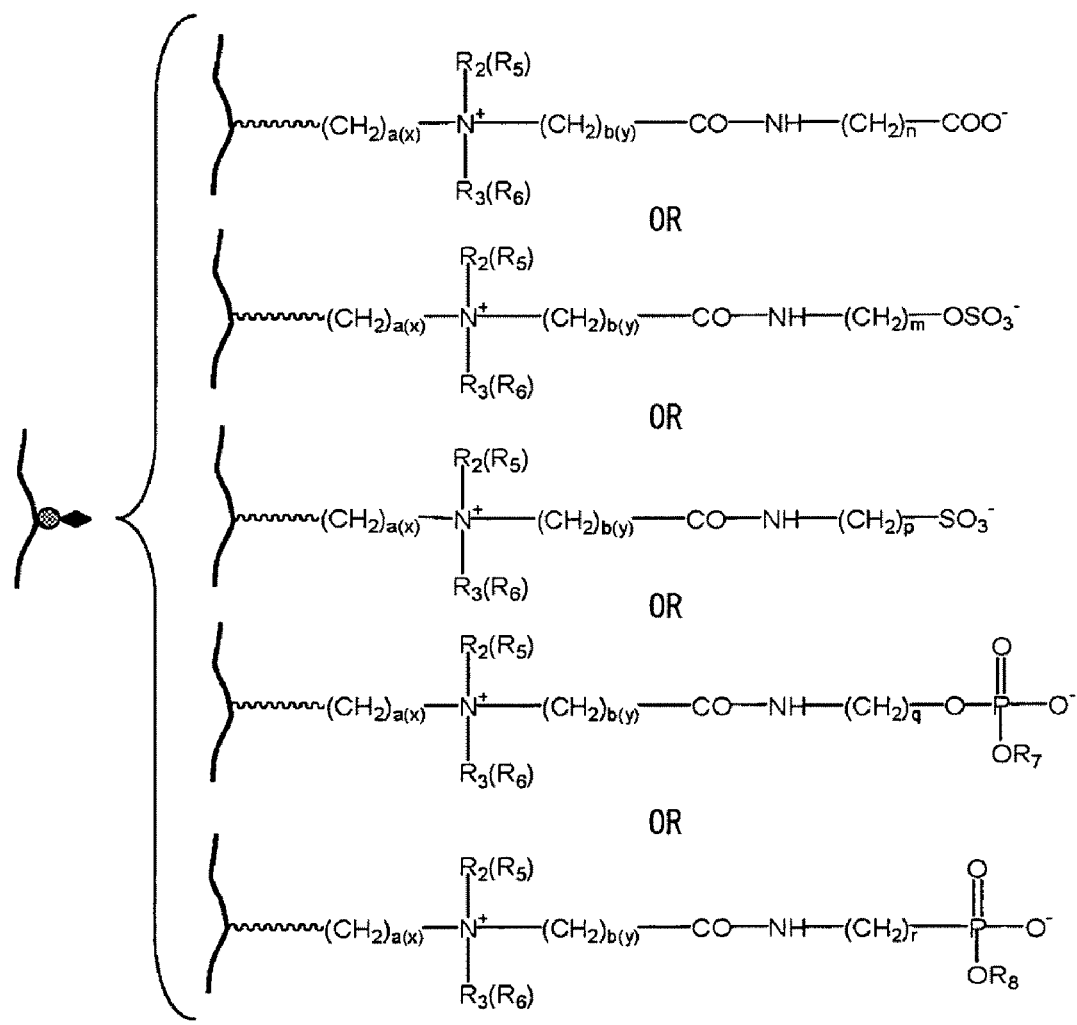

As shown in FIG. 1A, the structure according to the first aspect comprises a substrate 1, polymers 2 present on the substrate surface, first target substance capturing molecules (first trapping molecules) 5 bonded to the polymers 2, and protective molecules 4.

Each component of this configuration will be described below.

(Substrate)

The substrate 1 functions as a support body for the structure, and the polymers 2 can be formed on the substrate surface.

Any material can be used for the substrate 1, provided that the substrate can function as the support body for the structure in accordance with the present invention. Examples of preferred materials include metals such as gold, silver, copper, platinum, and aluminum, semiconductors such as CdS and ZnS, and metal oxides such as titanium oxide and aluminum oxide that can be bonded to amino groups or thiol groups, or glass, silicon, titanium oxide, and ceramics that can be bonded to silanol groups, or ceramics and carbon that can be bonded to carboxyl groups. Plastics on which carboxyl groups can be provided by oxidizing the surface by oxygen plasma treatment or UV treatment may be also used.

The substrate 1 may have any shape, for example, the shape of a flat plate, a powder, or a microstructure. The shape of substrate 1 may be that of a flat plate, bent plate, powder, microstructure, or a microtiter plate.

(Polymer)

The polymer 2 is a polymer of the carboxybetaine monomer represented by General Formula (1).

One end group of the polymer of the carboxybetaine monomer represented by General Formula (1) is immobilized onto the substrate 1, and an intramolecular salt structure (amphoteric ion) preventing nonspecific adsorption of biomolecules is present in the side chain of the polymer. Thus, the side chain of the polymer of the monomer represented by General Formula (1) is a carboxybetaine structure, in other words, an intramolecular salt structure having a quaternary ammonium cation and a carboxyl group anion in a molecule, and such intramolecular salt structure has an excellent ability of preventing nonspecific adsorption of impurities and the like contained in the analyte. In the description below a membrane of the polymers 2 formed with a high density on the surface of the substrate 1 will be called a nonspecific adsorption preventing membrane 14.

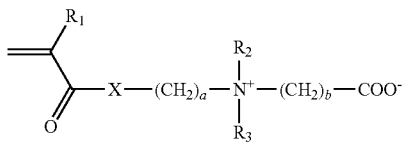

(1)

(in this formula, $R_1$ is a hydrogen atom or a methyl group; $R_2$ and $R_3$ are independently selected from a methyl group, an ethyl group, an n-propyl group, and an iso-propyl group; X is an oxygen atom or NH; a is an integer from 1 to 5; b is an integer equal to or larger than 1 and equal to or smaller than 4).

In other words, the compound represented by General Formula (1) is the compound represented by General Formula (3) or General Formula (4) below.

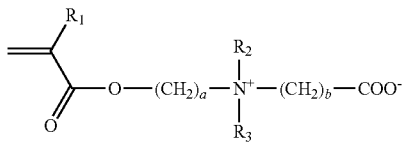

(3)

(in the formula, $R_1$ is a hydrogen atom or a methyl group; $R_2$ and $R_3$ are independently selected from a methyl group, an ethyl group, an n-propyl group, and an iso-propyl group; a is an integer from 1 to 5; b is an integer from 1 to 4).

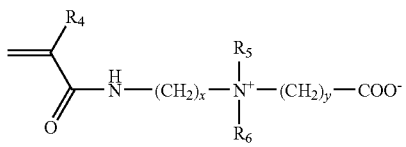

(4)

(in the formula, $R_4$ is a hydrogen atom or a methyl group; $R_5$ and $R_6$ are independently selected from a methyl group, an ethyl group, an n-propyl group, and an iso-propyl group; x is an integer from 1 to 5; y is an integer from 1 to 4).

The number-average molecular weight of the polymer 2 on the substrate 1 is equal to or higher than 5000 and equal to or lower than 1,000,000, preferably equal to or higher than 10,000 and equal to or lower than 1,000,000. The molecular weight distribution is preferably equal to or higher than 1 and less than 2. The density of polymers is preferably equal to or higher than 0.1 mol/nm$^2$.

One end group of the polymer 2 may be immobilized onto the substrate 1 by bringing the already synthesized polymer 2 into contact with the surface of substrate 1, but it is preferred that the configuration be synthesized by polymerization, more preferably that the polymerization be a living radical polymerization. The living radical polymerization will be described below.

Further, the first target substance capturing molecules 5 are immobilized onto some of the carboxyl groups 3 contained in the nonspecific adsorption preventing membrane 14, and the compound represented by General Formula (2) is bonded to at least some of other carboxyl groups 3. FIG. 1B shows a state in which protective molecules 4 are bonded to a carboxyl group 3 located in the side chain of the polymer 2. A method for immobilizing the first target substance capturing molecules and a method for immobilizing the compound represented by General Formula (2) will be described below.

(Living Radical Polymerization)

When b in General Formula (1) is 1, the carboxybetaine monomer represented by General Formula (1) can be synthesized referring to Gaofenzi Cailiao Kexue Yu Gongcheng (2000), 16(6), 44 to 46. Thus, the target carboxybetaine monomer can be obtained by reacting a (meth)acrylic acid ester or (meth)acrylamide with sodium chloroacetate.

On the other hand, when b in General Formula (1) is equal to or larger than 2, the synthesis can be conducted referring to J. Polym. Sci., Part A: Polym. Chem. 1997, 35, 3527 to 3536. Thus, the target carboxybetaine monomer can be obtained by reacting a (meth)acrylic acid ester or (meth)acrylamide with a lactone.

Polymers synthesized by living radical polymerization typically have a narrow molecular weight distribution, and a polymer layer can be grafted with a high density onto a substrate. Therefore, in accordance with the present invention, where the carboxybetaine monomer represented by General Formula (1) or (2) is polymerized, a nonspecific adsorption preventing membrane formed by the polymer with a high density can be provided on the substrate, and the first target substance capturing molecules can be immobilized onto at least some of carboxyl groups of the nonspecific adsorption preventing membrane. Examples of living radical polymerization methods include atom transfer radical polymerization (ATRP) in which an organic halide serves as an initiator and a transition metal complex serves as a catalyst, nitroxide mediated polymerization (NMP), which uses a radical trapping agent such as a nitroxide compound, and photo-initiated polymerization using a radical trapping agent such as dithiocarbamate. In accordance with the present invention, the structure may be produced by any of these methods, but from the standpoint of easiness of control, it is preferred that the atom transfer radical polymerization be used.

A method for forming the polymer on the substrate surface will be described below.

(Atom Transfer Radical Polymerization)

When the living radical polymerization is atom transfer radical polymerization, organic halides such as represented by Chemical Formulas 1 through 3, or halogenated sulfonyl compounds represented by Chemical Formula 4 can be used as polymerization initiators.

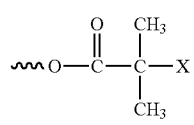

(Chemical Formula 1)

(X: halogen atom)

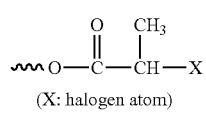

(Chemical Formula 2)

(X: halogen atom)

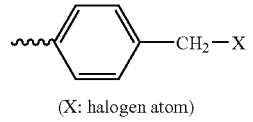

(Chemical Formula 3)

(X: halogen atom)

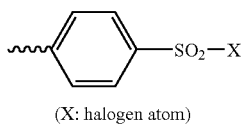

(Chemical Formula 4)

(X: halogen atom)

The atom transfer radical polymerization is performed by placing a substrate having an atom transfer radical polymerization initiator introduced therein in a reaction solvent, adding the carboxybetaine monomer represented by General Formula (1) that will form a nonspecific adsorption preventing membrane in polymerization and a transition metal complex, and replacing the reaction system atmosphere with an inert gas. As a result, the polymerization can be conducted, while maintaining a constant graft density. In other words, the polymerization is conducted in a living mode, and all the polymers can grow almost uniformly on the substrate.

The reaction solvent is not particularly limited and, for example, the following solvents can be used: dimethylsulfoxide, dimethylformamide, acetonitrile, pyridine, water, methanol, ethanol, propanol, butanol, pentanol, hexanol, heptanol, cyclohexanol, methyl cellosolve, ethyl cellosolve, iso-propyl cellosolve, butyl cellosolve, acetone, methyl ethyl ketone, methyl isobutyl ketone, cyclohexanone, ethyl acetate, butyl acetate, ethyl propionate, trioxane, and tetrahydrofuran. These solvents may be used individually or in combinations of two or more thereof.

Nitrogen gas or argon gas can be used as the inert gas.

The transition metal complex used in the reaction is composed of a metal halide and a ligand. A metal of the metal halide is preferably a transition metal selected from Ti with an atomic number of 22 to Zn with an atomic number of 30. The especially preferred metals are Fe, Co, Ni, and Cu. The preferred among the metal halides are copper (I) chloride and copper (I) bromide.

The ligand is not particularly limited, provided that it can be coordinated with the metal halide. Examples of suitable ligands include 2,2'-bipyridyl, 4,4'-di-(n-heptyl)-2,2'-bipyridyl, 2-(N-pentyliminomethyl)pyridine, (−)-sparteine, tris(2-dimethylaminoethyl)amine, ethylenediamine, dimethylglyoxime, 1,4,8,11-tetramethyl-1,4,8,11-tetraazacyclotetradecane, 1,10-phenanthroline, N,N,N',N'',N''-pentamethyldiethylenetriamine, and hexamethyl(2-aminoethyl)amine.

The amount of the transition metal complex added is 0.001 wt. % to 10 wt. %, preferably 0.05 wt. % to 5 wt. %, based on the carboxybetaine monomer that will constitute the nonspecific adsorption preventing membrane.

The polymerization temperature is within a range from 10° C. to 100° C., preferably 20° C. to 80° C.

Further, when the polymerization is performed, a free polymerization initiator that is not immobilized onto the substrate may be also added. A free polymer produced from the free polymerization initiator can serve as an indicator of the molecular weight and molecular weight distribution of the polymers grafted onto the substrate.

It is preferred that a free polymerization initiator identical to the atom transfer radical polymerization initiator that is immobilized onto the substrate be selected. Accordingly, it is preferred that the free polymerization initiator be ethyl 2-bromoisobutyrate with respect to the polymerization initiator of Chemical Formula 1 (X=Br). Further, it is preferred that the free polymerization initiator be ethyl 2-bromopropionate with respect to the polymerization initiator of Chemical Formula 2 (X=Br).

The substrate that has a polymer grafted thereonto and a nonspecific adsorption preventing membrane formed thereon can be obtained by washing the substrate thoroughly with the above-described reaction solvent upon completion of polymerization.

(Nitroxide-Mediated Polymerization)

When the living radical polymerization is a nitroxide-mediated polymerization, nitroxide compounds such as represented by Chemical Formulas 5 to 7 can be used as the polymerization initiators.

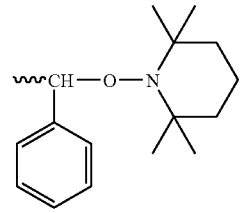

Chemical Formula 5

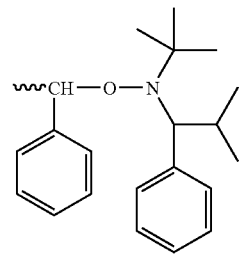

Chemical Formula 6

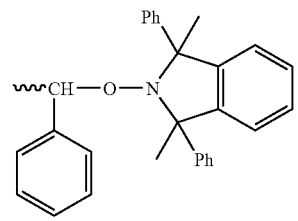

Chemical Formula 7

The nitroxide-mediated polymerization is performed by placing a substrate having a nitroxide-mediated polymerization initiator introduced therein in a reaction solvent, adding the carboxybetaine monomer represented by General Formula (1) as the monomer of the polymer molecules which form a nonspecific adsorption preventing membrane, and replacing the reaction system atmosphere with an inert gas. As a result, the polymerization can be conducted, while maintaining a constant graft density. In other words, the polymerization is conducted in a living mode, and all the polymers can grow almost uniformly on the substrate.

The reaction solvent is not particularly limited, and the above-described solvents can be used. The solvents can be used individually or in combination of two or more thereof.

Nitrogen gas or argon gas can be used as the inert gas.

The polymerization temperature is within a range from 10° C. to 120° C., preferably from 20° C. to 100° C. Where the polymerization temperature is below 10° C., the obtained nonspecific adsorption preventing membrane has a low molecular weight or the polymerization process is hindered.

Further, when the polymerization is performed, a free polymerization initiator that is not immobilized onto the substrate may be also added.

A free polymer produced from the free polymerization initiator can serve as an indicator of the molecular weight and molecular weight distribution of the polymer grafted onto the substrate.

It is preferred that a free polymerization initiator identical to the nitroxide-mediated polymerization initiator that is immobilized onto the substrate be selected. Accordingly, it is preferred that the free polymerization initiator be a nitroxide compound represented by Chemical Formula 8 with respect to the polymerization initiator of Chemical Formula 5.

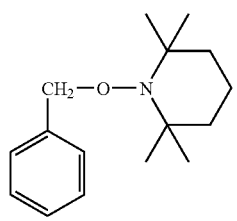

Chemical Formula 8

The substrate that has polymers grafted thereonto can be obtained by washing the substrate thoroughly with the above-described reaction solvent upon completion of polymerization.

(Photoinitiated Polymerization)

When the living radical polymerization is a photoinitiated polymerization, an N,N-dithiocarbamine compound such as represented by Chemical Formula 9 can be used as the polymerization initiator.

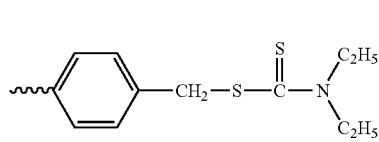

Chemical Formula 9

The photoinitiated polymerization is performed by placing a substrate having a photoinitiated polymerization initiator introduced therein in a reaction solvent, adding the carboxybetaine monomer represented by General Formula (1) that will form a nonspecific adsorption preventing membrane, replacing the reaction system atmosphere with an inert gas and having the reaction system irradiated with light. As a result, the polymerization can be conducted, while maintaining a constant graft density. In other words, the polymerization is conducted in a living mode, and all the polymers can grow almost uniformly on the substrate.

The reaction solvent is not particularly limited, and the above-described solvents can be used. The solvents can be used individually or in combination of two or more thereof.

Nitrogen gas or argon gas can be used as the inert gas.

The wavelength of the light used for irradiation differs depending on the type of the photoinitiated polymerization initiator used. Where a polymer is grafted onto a substrate surface having a photoinitiated polymerization initiator such as represented by Chemical Formula 9, the photoinitiated polymerization will effectively proceed when the reaction system is irradiated with light having a wavelength of 300 nm to 600 nm.

In order to suppress side reactions, it is preferred that the polymerization be performed at room temperature or a lower temperature. Within a temperature range in which the same effect is obtained, no particular limitation is placed on the temperature interval.

Further, when the polymerization is performed, a free polymerization initiator that is not immobilized onto the substrate may be also added. A free polymer produced from the free polymerization initiator can serve as an indicator of the molecular weight and molecular weight distribution of the polymer grafted onto the substrate.

It is preferred that a free polymerization initiator identical to the photoinitiated polymerization initiator that is immobilized onto the substrate be selected. Accordingly, it is preferred that the free polymerization initiator be a dithiocarbamate compound represented by Chemical Formula 10 with respect to the polymerization initiator of Chemical Formula 9.

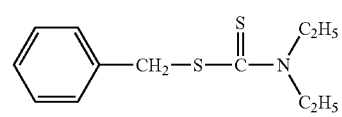

Chemical Formula 10

The substrate that has a polymer grafted thereonto can be obtained by washing the substrate thoroughly with the above-described reaction solvent upon completion of polymerization.

In the present invention, the method for immobilizing the polymerization initiator onto the substrate surface is not particularly limited, but if the substrate is a metal, a method is preferred by which a polymerization initiator containing a thiol compound is bonded to the substrate surface, or a polymerization initiator is bonded after the substrate has been pretreated with a thiol compound.

Where the substrate is a metal having an oxide film, a method is preferred by which a polymerization initiator containing a silane coupling agent is bonded, or a polymerization initiator is bonded after the substrate has been pretreated with a silane coupling agent.

Where the substrate is a plastic, a method is preferred by which a polymerization initiator containing an amino compound is bonded after the surface has been oxidized by oxygen plasma treatment, UV treatment or the like to develop carboxyl groups, or a polymerization initiator is bonded after the surface has been pretreated with an amino compound.

(First Target Substance Capturing Molecule)

The target substance capturing molecule 5 is a molecule that performs trapping or transformation by interaction with the target substance. Examples of a suitable target substance capturing molecule 5 include nucleic acids, proteins, sugar chains, lipids, and complexes thereof. More specific examples include, but are not limited to, DNA, RNA, aptamers, genes, chromosomes, cell membranes, viruses, antigens, antibodies, antibody fragments, lectins, haptens, hormones, receptors, enzymes, peptides, sphingoglycolipids, and sphingolipids. Among them antibodies, antibody fragments, or enzymes capable of trapping or transforming biosubstances are preferred.

A method by which the first target substance capturing molecules 5 are covalently bonded to at least some of carboxyl groups 3 in the side chains of the polymers 2 can be used for immobilizing the first target substance capturing molecules onto the substrate 1.

More specifically, after the polymer of the carboxybetaine monomer represented by General Formula (1) has been formed as shown by Reaction Equation 1, active esterification is performed by using N-hydroxysulfosuccinimide (NHS), 1-ethyl-3-(3-dimethylaminopropyl)carbodiimide (EDC) or the like at the carboxyl groups of side chain and replacing the carboxyl groups of the side chains of the polymers with succinimido groups. The first target substance capturing molecules can be immobilized onto the side chains of the polymers by reacting an amino group of the first target substance capturing molecule with the succinimido group (active ester group).

(Reaction Equation 1)

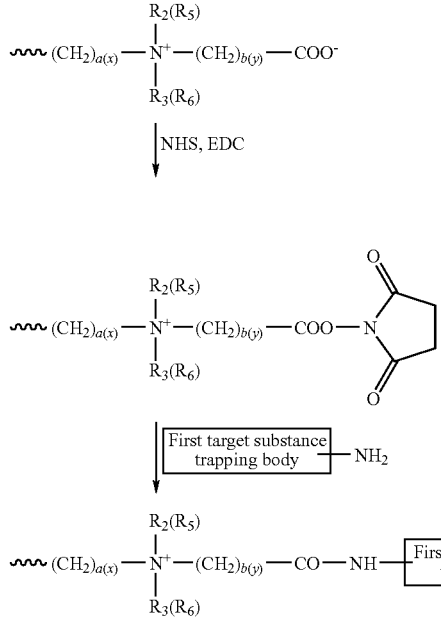

(Deactivation of Succinimido Group)

After the first target substance capturing molecules have been immobilized onto the polymers, the unreacted succinimido groups (active ester groups) of the polymers are reacted with Compound 4 represented by General Formula (2) and the succinimido groups (active ester groups) are deactivated.

The Compound 4 represented by General Formula (2) is a compound represented by any of General Formulas (5) to (9) below.

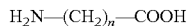 (5)

In General Formula (5), n is an integer from 1 to 4 and limited by b of General Formula (1), and n+b is an integer from 2 to 5. The hydrogen atom of the methylene group may be substituted with a hydroxyl group, a methyl group, or a hydroxymethyl group.

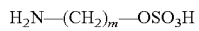 (6)

In General Formula (6), m is an integer from 1 to 4 and limited by b of General Formula (1), and m+b is an integer from 2 to 5. The hydrogen atom of the methylene group may be substituted with a hydroxyl group, a methyl group, or a hydroxymethyl group.

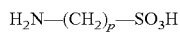 (7)

In General Formula (7), p is an integer from 1 to 4 and limited by b of General Formula (1), and p+b is an integer from 2 to 5. The hydrogen atom of the methylene group may be substituted with a hydroxyl group, a methyl group, or a hydroxymethyl group.

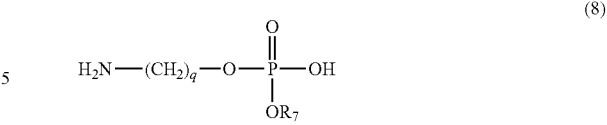 (8)

In General Formula (8), $R_7$ is a methyl group or an ethyl group. In General Formula (8), q is an integer from 1 to 4 and limited by b of General Formula (1), and q+b is an integer from 2 to 5. The hydrogen atom of the methylene group may be substituted with a hydroxyl group, a methyl group, or a hydroxymethyl group.

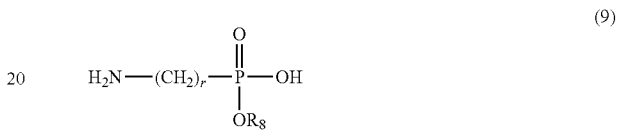 (9)

In General Formula (9), $R_8$ is a methyl group or an ethyl group. In General Formula (9), r is an integer from 1 to 4 and limited by b of General Formula (1), and r+b is an integer from 2 to 5. The hydrogen atom of the methylene group may be substituted with a hydroxyl group, a methyl group, or a hydroxymethyl group.

Therefore, the unreacted succinimido groups (active ester groups) of the polymers are reacted with compounds represented by General Formulas (5) to (9) according to the reactions of Reaction Equations 2 to 6 to deactivate the succinimido groups (active ester groups).

(Reaction Equation 2)

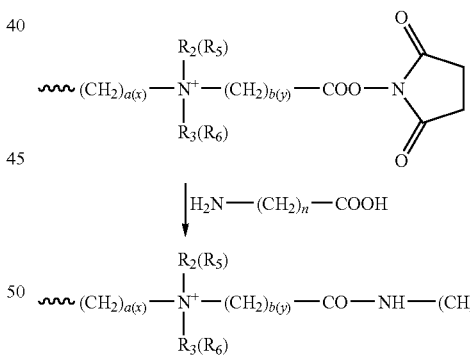

(Reaction Equation 3)

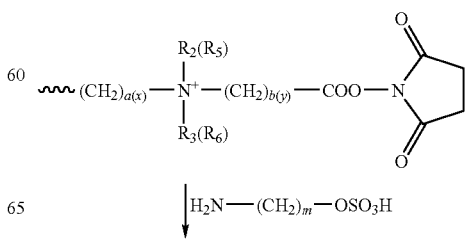

-continued

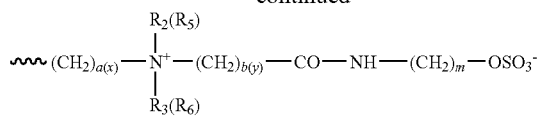

(Reaction Equation 4)

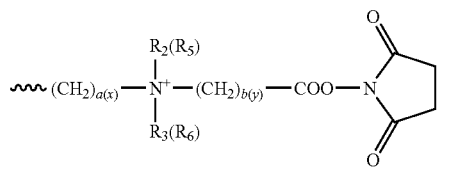

(Reaction Equation 5)

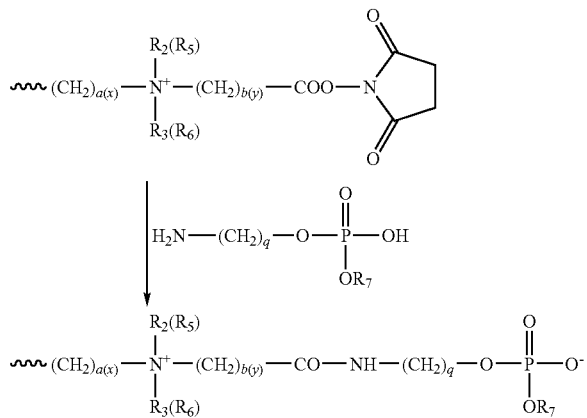

(Reaction Equation 6)

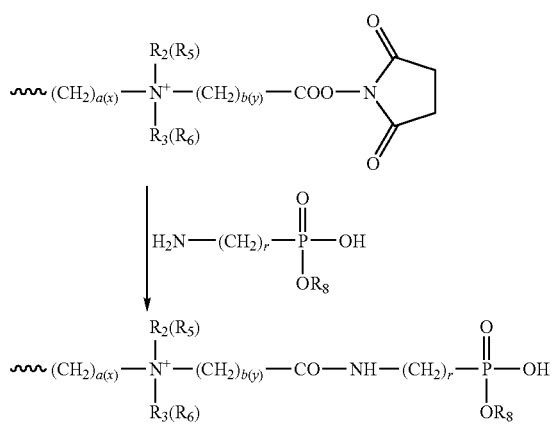

(Target Substance Detection Element)

The second aspect of the present invention will be described below.

The second aspect of the present invention resides in a target substance detection element having a substrate having a detection region, polymers present on a surface of the substrate, and first target substance capturing molecules bonded to the polymers, wherein the polymer comprises a polymer of a carboxybetaine monomer represented by General Formula (1) below;

the first target substance capturing molecules are bonded to some of the carboxyl groups of the polymers; and a compound represented by General Formula (2) is bonded to at least some of the carboxyl groups, from among the carboxyl groups of the polymers, that are not bonded to the first target substance capturing molecules.

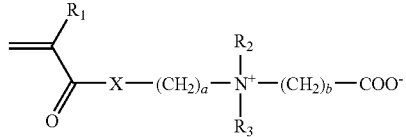

(1)

(in this formula, $R_1$ is a hydrogen atom or a methyl group; $R_2$, $R_3$ are independently selected from a methyl group, an ethyl group, an n-propyl group, and an iso-propyl group; X is an oxygen atom or NH; a is an integer from 1 to 5; b is an integer equal to or larger than 1 and equal to or smaller than 4).

$$H_2N—(CH_2)_n—Y \qquad (2)$$

(in this formula, n is an integer equal to or larger than 1 and equal to or smaller than 4, such that n+b is an integer from 2 to 5; Y is any group from among —COOH, —OSO$_3$H, —SO$_3$H, —OPO(OH)(OR$_7$), —PO(OH)(OR$_8$) (R$_7$ and R$_8$ are each independently a methyl group or an ethyl group); the hydrogen atom of the methylene group may be substituted with a hydroxyl group, a methyl group, or a hydroxymethyl group).

Figure 2:
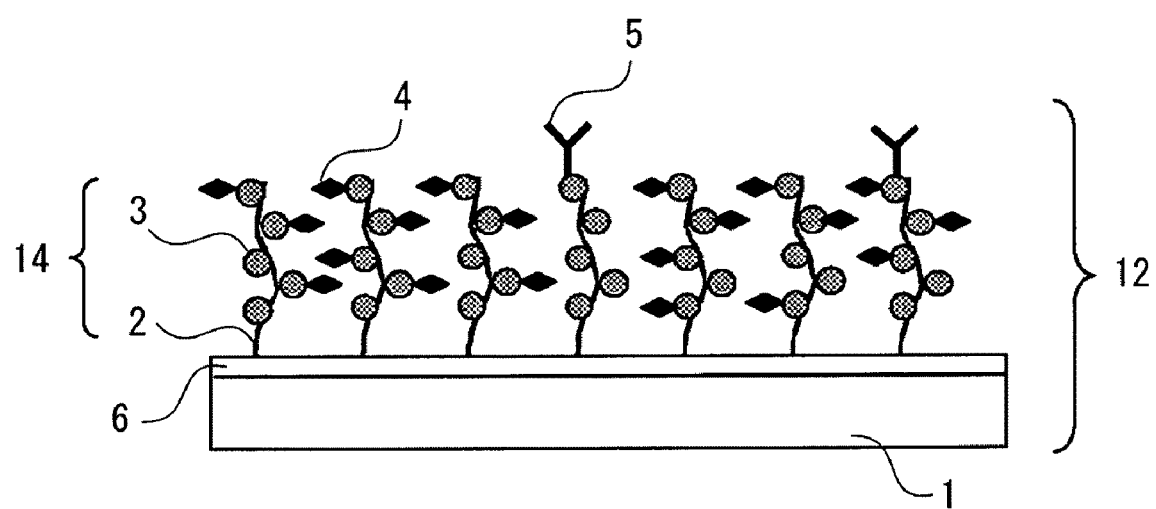
FIG. 2 is a schematic drawing illustrating an example of the target substance detection element in accordance with the present invention.

FIG. 2 is a schematic drawing illustrating the target substance detection element 12 according to the second aspect of the present invention.

The substrate 1 has a detection region 6.

The detection region 6 is a region for detecting the trapped target substance. The detection region 6 is composed of a material that transfers signals derived from the trapped target substance. For example, where the detection method uses surface plasmon resonance (SPR) or local plasmon resonance (LSPR), a material generating surface plasmons is contained on the surface. Where the detection method uses a quartz oscillator microbalance (QCM), a material that changes the frequency proportionally to the weight of the adsorbed substance is contained on the surface. Where the detection method uses a field-effect transistor (FET), the region is configured by a material capable of conducting an electric current and suitable for micromachining. Where the detection method is a magnetic detection method, a material that can lose or inverse magnetic polarity comparatively easily, such as soft magnetic material, can be contained on the surface. Where the detection method is an electrochemical detection method, it is preferred that the surface be formed from a material having a wide electric potential region that does not inhibit electrochemical reactions. Where the detection method is based on light absorption, the surface is preferably from a material that transmits the light of detection wavelength. Where the detection method is based on fluorescence or luminescence, it is preferred that the material does not absorb the light of detection wavelength.

Examples of suitable materials for the detection region 6 include gold, silver, copper, platinum, quartz, silicon, germanium, zinc oxide, titanium oxide, silicon oxide, indium oxide, cadmium sulfide, cadmium selenide, gallium arsenide, Permalloy (Ni—Fe alloy), Co—Fe—B alloys, mercury, carbon, diamond, glass, or plastics, but this list is not limiting.

The selection of a material for the detection region 6 is mainly determined by the method for detecting the target substance. When SPR is used as the detection method, the material of the detection region 6 is preferably a metal such as gold, silver, copper, or platinum. The preferred among them is gold. When a QCM is employed in the detection method, the material of the detection region 6 is preferably quartz. When a FET is used as the detection method, examples of materials suitable for the detection region 6 include silicon, germanium, zinc oxide, titanium oxide, silicon oxide, indium oxide, cadmium sulfide, cadmium selenide, and gallium arsenide. Where SPR, QCM, or FET is used as the detection method, as described hereinabove, the target substance can be detected without labeling.

When a magnetic detection method is used as the detection method, the material of the detection region 6 is preferably a soft magnetic material such as Permalloy (Ni—Fe alloy) or a Co—Fe—B alloy. When the detection method is an electrochemical detection method, the material of the detection region 6 is preferably gold, platinum, mercury, carbon, or diamond. When the detection method uses light absorption, fluorescence, or luminescence, the material of the detection region 6 is preferably glass or plastic.

The detection region 6 may be present on the surface of the substrate 1, or inside the substrate 1. For example, SPR and electrochemical detection method represent cases in which the detection region 6 is present on the surface of the substrate 1. With the SPR, a thin metal film generating surface plasmons is formed on the substrate surface. With electrochemical detection, a metal is formed at least on the surface of working electrode.

On the other hand, QCM, FET, and magnetic sensors represent cases in which the detection region 6 may be also present inside the substrate 1. With a QCM, a target substance detection element can be fabricated by forming a nonspecific adsorption preventing membrane on a thin gold film formed on a quartz surface. With a FET, the target substance detection element in accordance with the present invention can be produced by forming a nonspecific adsorption preventing membrane on the surface of a structure composed of a material capable of conducting electric current. With a magnetic sensor, a target substance detection element can be produced by forming a nonspecific adsorption preventing membrane on a layer formed on the surface of a multilayer structure comprising Permalloy (Ni—Fe alloy) or a Co—Fe—B alloy.

FIG. 2 illustrates a case in which the substrate 1 has multiple layers and, from among these layers, a layer including the surface of the substrate 1 is the detection region 6, this case representing an example in which the surface of the substrate 1 is the detection region 6. However, the substrate 1 is not limited to this example, and a configuration may be used in which the detection region is a layer, from among a multiplicity of layers, that is not on the surface, or the substrate 1 may be formed by one layer and the entire substrate 1 may be the detection region 6.

The nonspecific adsorption preventing membrane 14 and first target substance capturing molecules 5 are identical to the nonspecific adsorption preventing membrane and first target substance capturing molecules of the first aspect of the present invention.

(Target Substance Detection Kit)

The third aspect of the present invention will be described below.

The third aspect of the present invention resides in a target substance detection kit comprising:

the target substance detection element according to the second aspect of the present invention; and a labeling material comprising a labeling substance and a second target substance capturing molecule.

Figure 3:
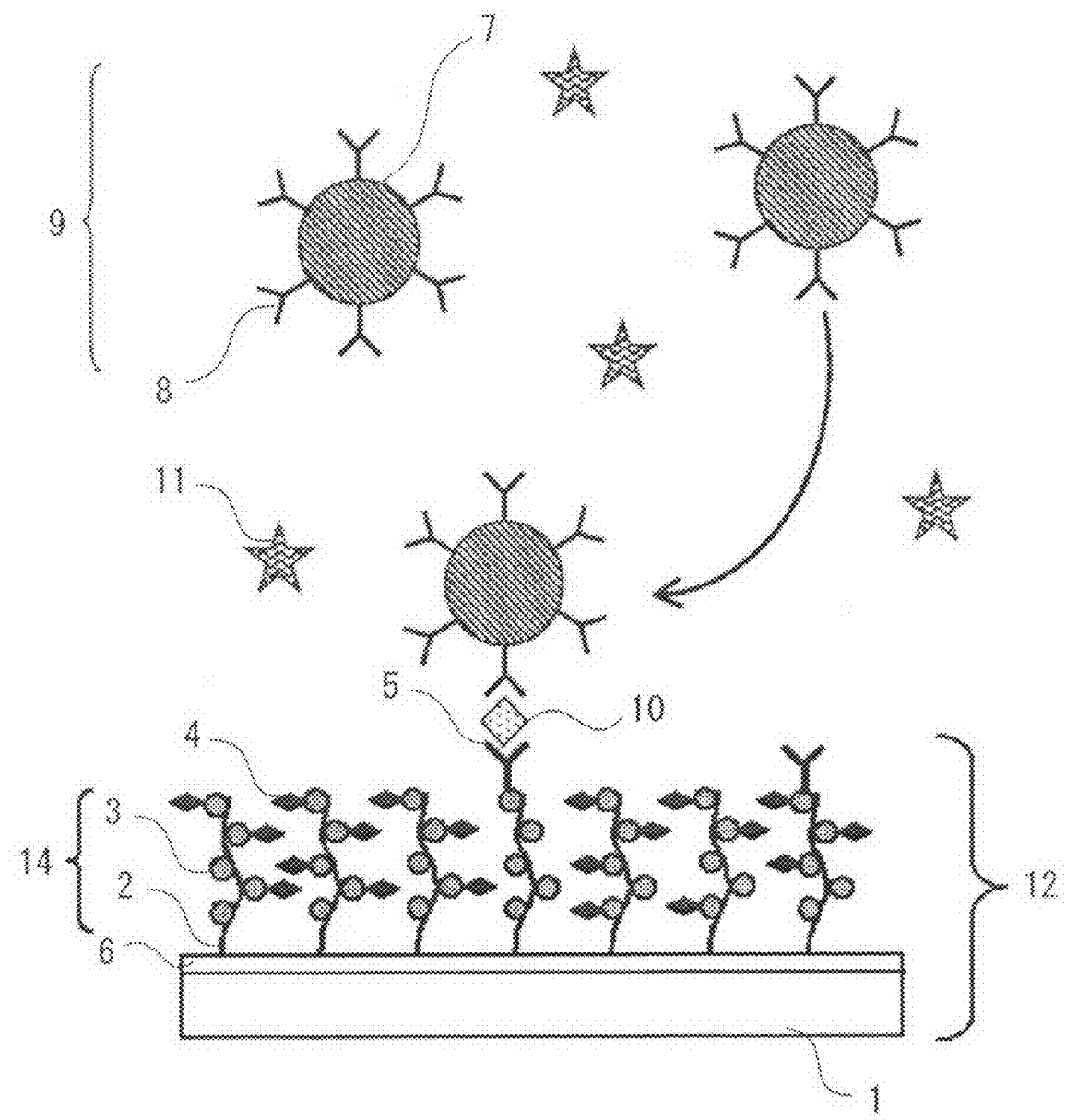
FIG. 3 is a schematic drawing illustrating an example of the target substance detection kit in accordance with the present invention.

FIG. 3 shows an example of the target substance detection kit according to the third aspect of the present invention.

The target substance detection kit comprises a target substance detection element 12 and a labeling material 9.

The target substance detection element 12 is identical to the target substance detection element that is the second aspect of the present invention, and the detection region 6 of the target substance detection element 12 is a detection region that can be sensitive to a labeling substance 7 of the labeling material 9. Contaminant 11 is a contaminant contained in the analyte.

The labeling material 9 includes a labeling substance 7 and a second target substance capturing molecule 8. The second target substance capturing molecule 8 may bind to the labeling substance 7, or may link to the surface of the labeling substance 7. When the second target substance capturing molecule 8 binds to the labeling substance 7, the bond between the second target substance capturing molecule 8 and the labeling substance 7 is preferably a covalent bond, or a coordination bond or a van der waals bond. The bond is more preferably a covalent bond or a coordination bond.

Examples of suitable labeling substances 7 include gold colloid, latex beads, luminal, ruthenium, enzymes, radioactive substances, fluorescent substance, and magnetic substances. Specific examples of fluorescent substances include quantum dots, fluorescent proteins (for example, GFP and derivatives thereof), Cy3, Cy5, Texas Red, fluorescein, and Alexa colorants (for example, Alexa 568). Specific examples of enzymes include horseradish peroxidase, alkali phosphatase, β-galactosidase, and luciferase. Examples of magnetic substances include ferrites. Ferrites are preferred because they have sufficient magnetic properties under physiologically active conditions and have high resistance to deterioration such as oxidation in solvents. Ferrites can be selected from magnetite ($Fe_3O_4$), maghemite ($\gamma$-$Fe_2O_3$), and composites obtained by replacing some of Fe in these compounds with other atoms. Examples of other atoms include Li, Mg, Al, Si, Ca, Sc, Ti, V, Cr, Mn, Co, Ni, Cu, Zn, Ga, Ge, Zr, Nb, Mo, Cd, In, Sn, Ta, and W. The labeling substance may also be a composite of the above-described materials.

The labeling substance 7 can have a particle, columnar, or star-like shape, but the particle shape is preferred. In the case of a particle shape, the mean particle size is preferably from 1 nm to 100 μm, more preferably from 3 nm to 10 μm. When the labeling substance is in the form of particles, the mean particle size is measured by a dynamic light scattering method.

Examples of suitable magnetic substances include Dynabeads marketed by Dynal, micromer-M, nanomag-D marketed by micromod, and Estapol marketed by Merck.

The second target substance capturing molecules 8 are immobilized onto the surface of the labeling substance 7 and have a function of trapping the target substance 10 in the same manner as the first target substance capturing molecules 5 of the target substance detection element 12. Therefore, examples of suitable second target substance capturing molecules 8 include the same materials as those of the first target substance capturing molecules 5. The second target substance capturing molecule 8 and the first target substance capturing molecule 5 have to trap different portions of the target substance 10. In this case, a composite is formed in which the target substance 10 is sandwiched between the second target substance capturing molecule 8 and first target substance capturing molecule 5. Further, for example, when the second target substance capturing molecule 8 and first target substance capturing molecule 5 are monoclonal antibodies, they have to be of different kinds. However, where the two are polyclonal antibodies, they may be of the same kind or of different kinds. In some cases, one of the two types of target substance capturing molecule is a monoclonal antibody and the other is a polyclonal antibody.

More specifically, the target substance 10 is trapped by the first target substance capturing molecule 5 disposed on the surface of the target substance detection element 12, and the target substance 10 trapped by the first target substance capturing molecule 5 is further trapped by the second target substance capturing molecule 8 of the labeling material 9. Thus, a composite of the first target substance capturing molecule 5—target substance 10—second target substance capturing molecule 8 structure is formed, and the labeling material 9 is disposed close to the detection region 6 of the target substance detection element 12. The labeling substance 7 of the labeling material 9 disposed close to the detection region 6 is detected by the detection region 6, and the detection of the labeling substance 7 in the detection region 6 is represented as a variation of an electric or physical signal of the target substance detection element 12. The presence of target substance or the number of target substances can be detected by using the variations in signals of the target substance detection element 12.

The description above is based on the assumption that the target substance 10 is trapped by the second target substance capturing molecule 8 after the target substance 10 has been trapped by the first target substance capturing molecule 5. However, after the target substance 10 has been trapped by the second target substance capturing molecule 8, the target substance 10 trapped by the second target substance capturing molecule 8 may be trapped by the first target substance capturing molecule 5.

The following combinations of such target substance detection element 12 and labeling substance 7 are possible. For example, where the target substance detection element 12 is a magnetic sensor element, it is preferred that the labeling substance 7 be a magnetic substance. Where the target substance detection element 12 is an electrode, it is preferred that the labeling substance 7 be an enzyme. Where the target substance detection element 12 is a microtiter plate, it is preferred that the labeling substance 7 be a gold colloid, a latex bead, luminol, ruthenium, enzyme, a radioactive substance, or a fluorescent substance.

As described hereinabove, where the target substance detection element 12 is a magnetic sensor element, the magnetic sensor element can detect the presence and number of magnetic substances located close to the detection region 6. In such case, an element having a detection region that detects the variations in magnetic properties, for example, a magnetoresistance effect element, a Hall effect element, and a superconducting quantum interference device can be advantageously used as the target substance detection element 12.

Ferrites can be used as magnetic substances. Ferrites are preferred because they have sufficient magnetic properties under physiologically active conditions and have high resistance to deterioration such as oxidation in solvents. Ferrites can be selected from magnetite ($Fe_3O_4$), maghemite ($\gamma\text{-}Fe_2O_3$), and composites obtained by replacing some of Fe in these compounds with other atoms. Examples of other atoms include Li, Mg, Al, Si, Ca, Sc, Ti, V, Cr, Mn, Co, Ni, Cu, Zn, Ga, Ge, Zr, Nb, Mo, Cd, In, Sn, Ta, and W.

EXAMPLES

The present invention will be described below in greater detail by using examples thereof, but the present invention is not limited to these examples, and the materials, compositions, reaction conditions, and the like can be freely changed within ranges in which magnetic biosensors having identical functions and effects are obtained.

Example 1

(1) Preparation of SPR Substrate

An Au film was immersed in an ethanol solution containing an atom transfer radical polymerization initiator represented by Chemical Formula 17 and the initiator was reacted with the Au film, thereby introducing the atom transfer radical polymerization initiator in the Au film surface in a gold film chip SIA Kit Au (manufactured by BIACORE).

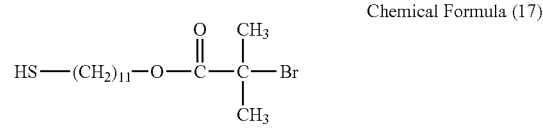

Chemical Formula (17)

The gold film chip having the atom transfer radical polymerization initiator introduced therein was then immersed in methanol, and then CuBr and 2,2'-bipyridyl were added. Oxygen contained in the reaction system was then removed by freeze vacuum degassing, the reaction atmosphere was replaced with nitrogen, and the carboxybetaine monomer represented by Chemical Formula 33 was reacted for a predetermined time by atom transfer radical polymerization. After the reaction, the membrane thickness of the polymer grafted onto the surface thereof was measured with a spectral ellipsometer (M-2000, manufactured by J. A. Woollam). The result was 17.1-18.2 nm (n=4).

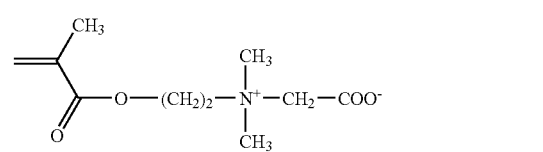

(Chemical Formula 33)

(2) Evaluation of Nonspecific Adsorption Preventing Capability of SPR

Figure 4:
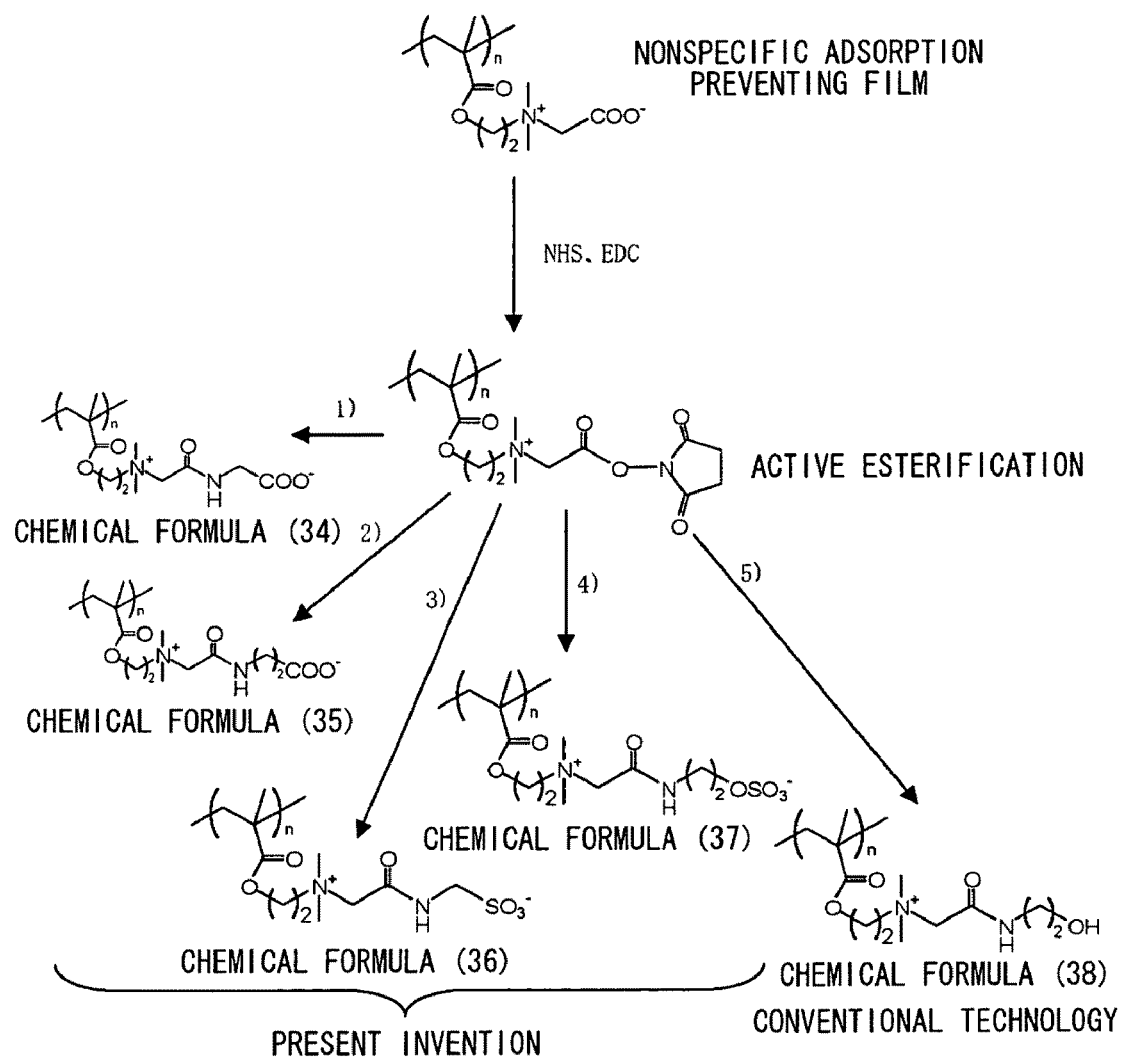
FIG. 4 is a reaction equation illustrating a method for deactivating a succinimide group contained in the nonspecific adsorption preventing membrane in accordance with the present invention.

The gold film chip prepared in Section (1) above was attached to an auxiliary sensor chip support and set in a sensor chip port of surface plasmon resonance (SPR) device BIACORE-X (manufactured by BIACORE), and the sensor chip was docked. A mixed solution of N-hydroxysuccinimide (NHS, 0.1 mM) and 1-ethyl-3-(3-dimethylaminopropyl)carbodiimide hydrochloride (EDC, 0.4 mM) was injected using an auto pipette from a sample addition position of a connector block of the SPR device, and the injection was conducted for 7 min at a flow velocity of 5 μL/min. Succinimide groups were thus introduced in the carboxyl groups contained in the nonspecific adsorption preventing membrane. Then, a reagent for deactivating the succinimide groups was injected within 7 min at a flow velocity of 5 μL/min, and the succinimide groups contained in the nonspecific adsorption preventing membrane were thus deactivated. As shown in FIG. 4, 1) glycine, 2) β-alanine, 3) aminomethanesulfonic acid, 4) monoaminoethyl sulfate and in Comparative Example 1 based on the conventional technology, (5) aqueous solution of ethanolamine were introduced via individual flow channels as reagents for deactivating the succinimide groups.

Figure 5:
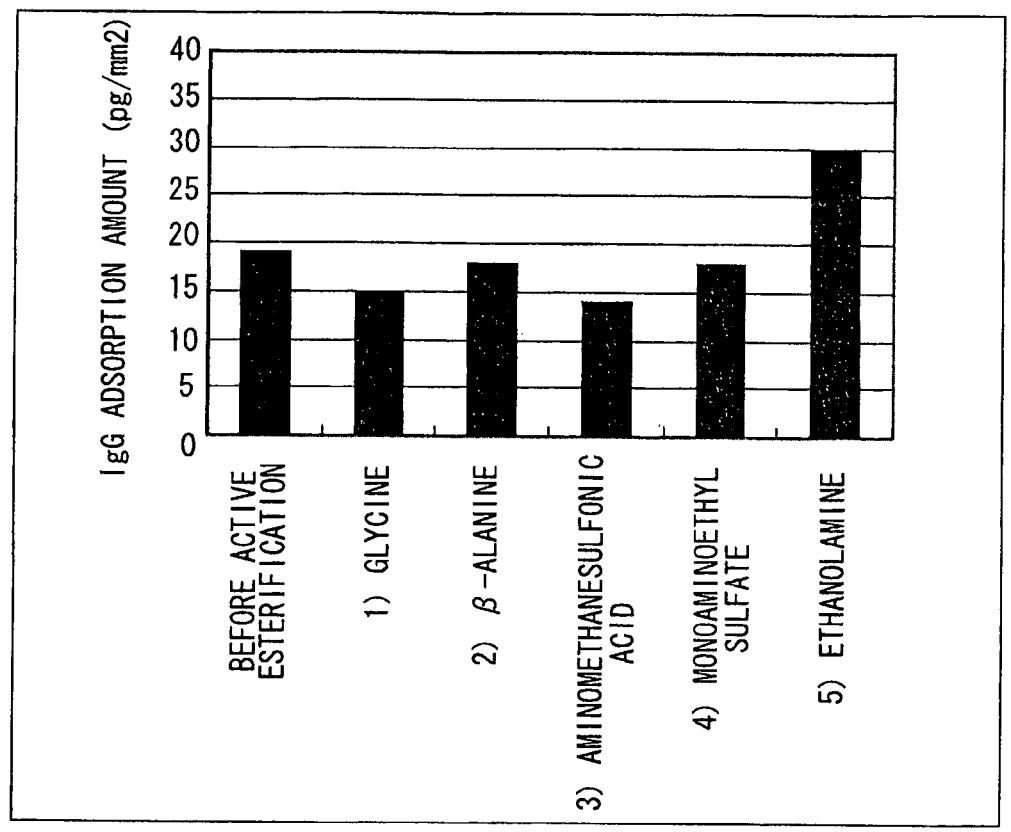
FIG. 5 is a graph illustrating a nonspecific adsorption amount of IgG in the nonspecific adsorption preventing membrane of Example 1.

After the sensorgram base has been confirmed to settle, a 1% Bovine-IgG solution (PBS, pH7.4) was injected within 2 min at a flow velocity of 20 μL/min, and a resonance signal variation (RU) in 5 min after completion of injection was measured. In the present SPR device, the variation caused by protein adsorption of 1 RU=1 pg/mm$^2$ could be measured and the measurement results are shown as nonspecific adsorption amount of IgG in FIG. 5. The results shown in FIG. 5 demonstrate that the nonspecific adsorption amount of IgG in the nonspecific adsorption preventing membrane represented by Chemical Formulas 34 to 37 in accordance with the present invention is less than that in the nonspecific adsorption preventing membrane represented by Chemical Formula 38 relating to the conventional technology. The improvement of the nonspecific adsorption preventing ability has thus been confirmed.

A structure and a magnetic biosensor can be obtained by the below-described methods.

Example 2

In the present example, a magnetic biosensor in which a nonspecific adsorption preventing membrane containing primary antibodies that trap PSA (Prostate-Specific Antigen) as a first target substance capturing molecule is formed in a detection region and a labeling material (magnetic label) composed of magnetite comprising secondary antibodies that trap PSA as the second target substance capturing molecule is fabricated and PSA is detected by using them as a magnetic biosensor. A magnetoresistance effect element is used as a detection system of the magnetic biosensor.

(1) Fabrication of Magnetic Marker

First, a labeling material having secondary antibodies that trap PSA as the second target substance capturing molecule is fabricated.

Magnetite particles (mean particle size 100 nm) are heat treated under a dry nitrogen atmosphere and then dispersed in anhydrous toluene. Aminopropyltrimethoxysilane, which is a silane coupling agent, is added to the magnetite particles—toluene dispersion system, and amino groups are introduced to the magnetite particle surface. Then, in order to immobilize the secondary antibodies that trap PSA as the second target substance capturing molecule, a glutalaldehyde crosslinking agent is used, the aforementioned amino groups and amino groups of the secondary antibodies are covalent bonded, and the second target substance capturing molecule can be immobilized on the magnetite particle surface.

The above-described operations make it possible to obtain a labeling material comprising the second target substance capturing molecule.

(2) Fabrication of Magnetic Biosensor

A magnetic biosensor is then fabricated that has formed in the detection region thereof a nonspecific adsorption preventing membrane that comprises primary antibodies that trap PSA as the first substance capturing molecule and maintains a neutral electric charge of the side chain of the polymer.

Figure 6:
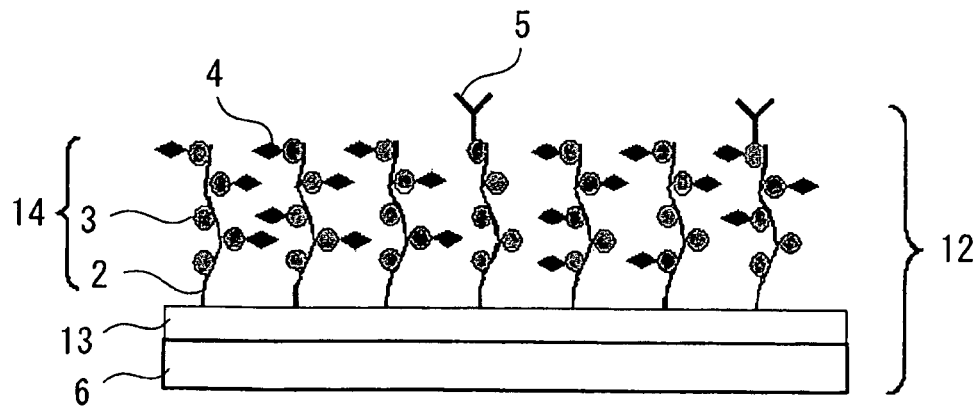
FIG. 6 is a schematic drawing illustrating an example of a magnetic sensor.

First, as shown in FIG. 6, an Au film 13 is formed on the upper surface of the magnetic detection region 6. In the present embodiment, because the magnetoresistance effect element is used as the detection system, the aforementioned detection region means a magnetoresistance effective film.

A nonspecific adsorption preventing membrane is then formed on the Au surface that is a detection region. An atom transfer radical polymerization initiator can be introduced in the Au film surface by immersing the Au film in an ethanol solution containing an atom transfer radical polymerization initiator represented by Chemical Formula 17 and reacting the initiator with the Au film.

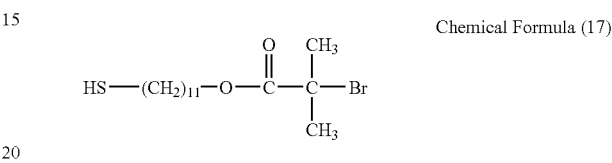

Chemical Formula (17)

The detection region having the atom transfer radical polymerization initiator introduced therein is then immersed in methanol, then ethyl 2-bromoisobutyrate is added as a free polymerization initiator, and CuBr and 2,2'-bipyridyl are added. Oxygen contained in the reaction system is then removed by freeze vacuum degassing, the reaction atmosphere is replaced with nitrogen, and the carboxybetaine monomer represented by Chemical Formula 11 is reacted for a predetermined time by atom transfer radical polymerization. The molecular weight and molecular weight distribution of the polymer produced from the ethyl 2-bromoisobutyrate used as a free polymerization initiator are measured. The number-average molecular weight is 97,000 and the molecular weight distribution is 1.15. These results can confirm that the graft polymers grafted onto the detection region are polymers with matching chain lengths.

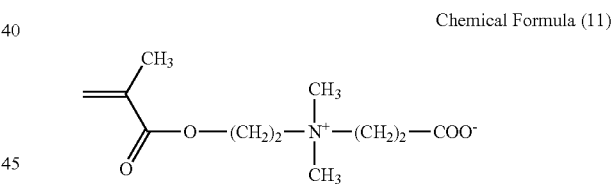

Chemical Formula (11)

The graft density of the polymers can be confirmed to be 0.65 mol/nm$^2$ by measuring the thickness and weight of the nonspecific adsorption preventing membrane formed in the detection region.

Primary antibodies that trap PSA are then immobilized as the first target substance capturing molecules on at least some of carboxyl groups contained in the nonspecific adsorption preventing membrane formed in the detection region. An aqueous solution of N-hydroxysulfosuccinimide and an aqueous solution of 1-ethyl-3-(3-dimethylaminopropyl)carbodiimide hydrochloride are coated in the same manner. By these operations, the carboxyl groups contained in the nonspecific adsorption preventing membrane are transformed into succinimide groups (active ester groups). The succinimide groups are reacted with amino groups of the primary antibodies, and the primary antibodies that trap PSA can be immobilized as the first target substance capturing molecules. Then, the unreacted succinimide groups contained in the nonspecific adsorption preventing membrane are deactivated by the compound represented by Chemical Formula 12 and can be converted into the intramolecular salt structure such as represented by Chemical Formula 13.

$$H_2N-CH_2-COOH \qquad \text{Chemical Formula (12)}$$

(Chemical Formula 13)

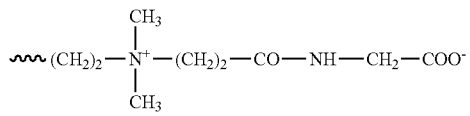

The above-described operations make it possible to fabricate a magnetic biosensor having a detection region comprising a nonspecific adsorption preventing membrane containing primary antibodies that trap PSA as the first target substance capturing molecules and maintaining a neutral electric charge of the side chain of the polymer.

(3) Detection of PSA

An attempt can be made to detect PSA that has been known as a marker of prostate cancer by using the magnetic marker and magnetic biosensor fabricated as described in sections (1) and (2) above, and conducting operations described below.

1) The detection region of the above-described magnetic biosensor is immersed in a phosphate buffer solution containing PSA that is the target substance (antigen) and also BSA and IgG as impurities.

2) The unreacted PSA and impurities are washed with the phosphate buffer solution.

3) The detection region of the magnetic biosensor subjected to the above-described processes 1) and 2) is immersed in a phosphate buffer solution containing the magnetic marker and incubated therein for 5 min.

4) The unreacted magnetic marker is washed with the phosphate buffer.

As a result of the above-described operations, the antigens are trapped by the primary antibodies and secondary antibodies, and the magnetic marker is immobilized in the detection region of the magnetic biosensor, as shown in FIG. 2. In other words, when no antigens are present in the analyte, the magnetic marker is not immobilized on the detection region of the magnetic biosensor. As a result, the detection of antigens can be performed by detecting the presence of the magnetic marker. Further, by detecting the number of the immobilized magnetic markers, it is possible to determine indirectly the number of antigens contained in the analyte. In the nonspecific adsorption preventing membrane of the detection region in the magnetic biosensor of the present example, a neutral electric charge of the side chain of the polymer is maintained. As a result, nonspecific adsorption of a target substance or impurities contained in the analyte can be prevented and the target substance can be detected with high sensitivity.

Example 3

The compound represented by Chemical Formula 12 of Example 2 is replaced with the compound represented by Chemical Formula 14, and the unreacted succinimide groups contained in the nonspecific adsorption preventing membrane are deactivated and converted into the intramolecular salt structure such as shown in Chemical Formula 15. Where the PSA detection is then performed in the same manner as in Example 2, a neutral electric charge of the side chain of the polymer is maintained in the nonspecific adsorption preventing membrane of the detection region in the magnetic biosensor. As a result, nonspecific adsorption of a target substance or impurities contained in the analyte can be prevented and the target substance can be detected with high sensitivity.

$$H_2N-(CH_2)_2-OSO_3H \qquad \text{Chemical Formula (14)}$$

Chemical Formula (15)

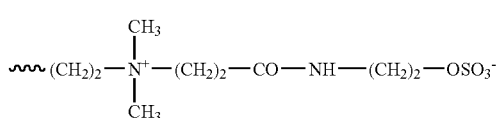

Example 4

The compound represented by Chemical Formula 12 of Example 2 is replaced with the compound represented by Chemical Formula 16, and the unreacted succinimide groups contained in the nonspecific adsorption preventing membrane are deactivated and converted into the intramolecular salt structure such as shown in Chemical Formula 17. Where the PSA detection is then performed in the same manner as in Example 2, a neutral electric charge of the side chain of the polymer is maintained in the nonspecific adsorption preventing membrane of the detection region in the magnetic biosensor. As a result, nonspecific adsorption of a target substance or impurities contained in the analyte can be prevented and the target substance can be detected with high sensitivity.

$$H_2N-(CH_2)_3-SO_3H \qquad \text{Chemical Formula (16)}$$

Chemical Formula (17)

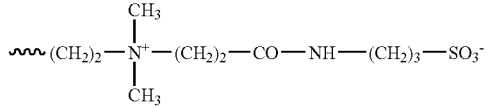

Example 5

The compound represented by Chemical Formula 12 of Example 2 is replaced with the compound represented by Chemical Formula 18, and the unreacted succinimide groups contained in the nonspecific adsorption preventing membrane are deactivated and converted into the intramolecular salt structure such as shown in Chemical Formula 19. Where the PSA detection is then performed in the same manner as in Example 2, a neutral electric charge of the side chain of the polymer is maintained in the nonspecific adsorption preventing membrane of the detection region in the magnetic biosensor. As a result, nonspecific adsorption of a target substance or impurities contained in the analyte can be prevented and the target substance can be detected with high sensitivity.

Chemical Formula (18)

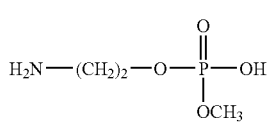

-continued

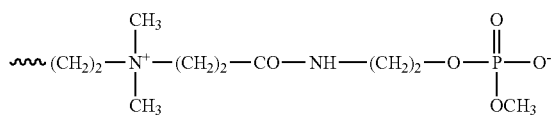

Chemical Formula (19)

Example 6

The compound represented by Chemical Formula 12 of Example 2 is replaced with the compound represented by Chemical Formula 20, and the unreacted succinimide groups contained in the nonspecific adsorption preventing membrane are deactivated and converted into the intramolecular salt structure such as shown in Chemical Formula 21. Where the PSA detection is then performed in the same manner as in Example 2, a neutral electric charge of the side chain of the polymer is maintained in the nonspecific adsorption preventing membrane of the detection region in the magnetic biosensor. As a result, nonspecific adsorption of a target substance or impurities contained in the analyte can be prevented and the target substance can be detected with high sensitivity.

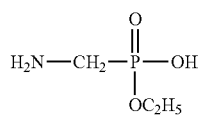

Chemical Formula (20)

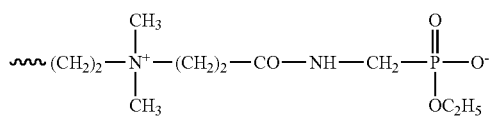

Chemical Formula (21)

Example 7

The carboxybetaine monomer (Chemical Formula 11) of Example 2 is replaced with the carboxybetaine monomer represented by Chemical Formula 22, the compound represented by Chemical Formula 12 is replaced with the compound represented by Chemical Formula 23, and the unreacted succinimide groups contained in the nonspecific adsorption preventing membrane are deactivated and converted into the intramolecular salt structure such as shown in Chemical Formula 24. The polymers of the present example have a number-average molecular weight of 89,000, a molecular weight distribution of 1.13, and a graft density of 0.68 mol/nm$^2$. Where the PSA detection is performed in the same manner as in Example 2, a neutral electric charge of the side chain of the polymer is maintained in the nonspecific adsorption preventing membrane of the detection region in the magnetic biosensor. As a result, nonspecific adsorption of a target substance or impurities contained in the analyte can be prevented and the target substance can be detected with high sensitivity.

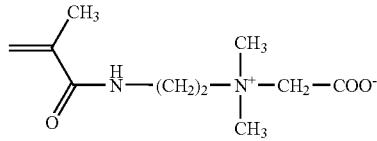

(Chemical Formula 22)

$H_2N$—$(CH_2)_2$—COOH (Chemical Formula 23)

(Chemical Formula 24)

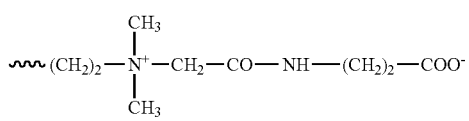

Example 8

The compound represented by Chemical Formula of Example 7 is replaced with the compound represented by Chemical Formula 25, and the unreacted succinimide groups contained in the nonspecific adsorption preventing membrane are deactivated and converted into the intramolecular salt structure such as shown in Chemical Formula 26. Where the PSA detection is then performed in the same manner as in Example 7, a neutral electric charge of the side chain of the polymer is maintained in the nonspecific adsorption preventing membrane of the detection region in the magnetic biosensor. As a result, nonspecific adsorption of a target substance or impurities contained in the analyte can be prevented and the target substance can be detected with high sensitivity.

$H_2N$—$CH_2$—$OSO_3H$

Chemical Formula (25)

Chemical Formula (26)

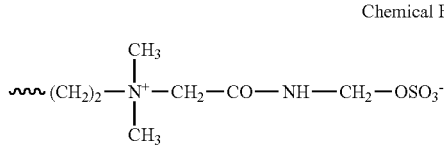

Example 9

The compound represented by Chemical Formula 23 of Example 7 is replaced with the compound represented by Chemical Formula 27, and the unreacted succinimide groups contained in the nonspecific adsorption preventing membrane are deactivated and converted into the intramolecular salt structure such as shown in Chemical Formula 28. Where the PSA detection is then performed in the same manner as in Example 7, a neutral electric charge of the side chain of the polymer is maintained in the nonspecific adsorption preventing membrane of the detection region in the magnetic biosensor. As a result, nonspecific adsorption of a target substance or impurities contained in the analyte can be prevented and the target substance can be detected with high sensitivity.

Chemical Formula (27)

$H_2N$—$CH_2$—$SO_3H$

Chemical Formula (28)

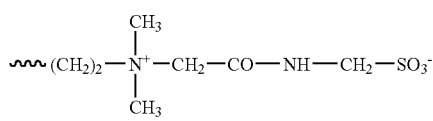

Example 10

The compound represented by Chemical Formula 23 of Example 7 is replaced with the compound represented by Chemical Formula 29, and the unreacted succinimide groups contained in the nonspecific adsorption preventing membrane are deactivated and converted into the intramolecular salt structure such as shown in Chemical Formula 30. Where the PSA detection is then performed in the same manner as in Example 7, a neutral electric charge of the side chain of the polymer is maintained in the nonspecific adsorption preventing membrane of the detection region in the magnetic biosensor. As a result, nonspecific adsorption of a target substance or impurities contained in the analyte can be prevented and the target substance can be detected with high sensitivity.

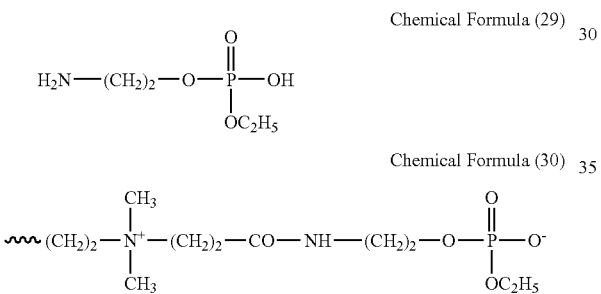

Chemical Formula (29)

Chemical Formula (30)

Example 11

The compound represented by Chemical Formula 23 of Example 7 is replaced with the compound represented by Chemical Formula 31, and the unreacted succinimide groups contained in the nonspecific adsorption preventing membrane are deactivated and converted into the intramolecular salt structure such as shown in Chemical Formula 32. Where the PSA detection is then performed in the same manner as in Example 7, a neutral electric charge of the side chain of the polymer is maintained in the nonspecific adsorption preventing membrane of the detection region in the magnetic biosensor. As a result, nonspecific adsorption of a target substance or impurities contained in the analyte can be prevented and the target substance can be detected with high sensitivity.

Chemical Formula (31)

Chemical Formula (32)

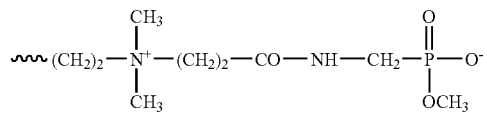

Comparative Example 2

The compound represented by Chemical Formula 12 of Example 2 is replaced with ethanolamine, and the unreacted succinimide groups contained in the nonspecific adsorption preventing membrane are deactivated. Where the detection of PSA is thereafter performed in the same manner as in Example 2, the electric charge of the side chain of the polymer shifts toward a positive charge, and such shift can be confirmed to cause the adhesion of impurities and deterioration of sensitivity with respect to that of Examples 2 through 11.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2007-217580, filed Aug. 23, 2007, which is hereby incorporated by reference herein in its entirety.

What is claimed is:

1. A structure having
   a substrate, polymers present on a surface of the substrate, and first target substance capturing molecules bonded to the polymers, wherein
   each of the polymers comprises a polymer of a carboxybetaine monomer represented by General Formula (1) below;
   the first target substance capturing molecules are bonded to some of the carboxyl groups of the polymers; and
   a compound represented by General Formula (2) is bonded to at least some of the carboxyl groups, from among the carboxyl groups of the polymers, that are not bonded to the first target substance capturing molecules

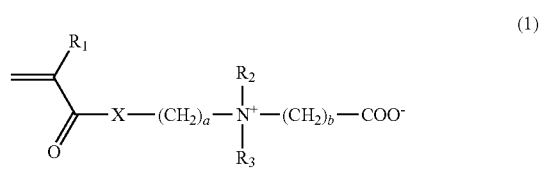

(1)

(in this formula, $R_1$ is a hydrogen atom or a methyl group; $R_2$ and $R_3$ are independently selected from a methyl group, an ethyl group, an n-propyl group, and an isopropyl group; X is an oxygen atom or NH; a is an integer from 1 to 5; b is an integer from 1 to 4)

$$H_2N—(CH_2)_n—Y \quad (2)$$

(in this formula, n is an integer from 1 to 4, such that n +b is an integer from 2 to 5; Y is $—OSO_3H$ or $—SO_3H$).

2. The structure according to claim 1, wherein the compound represented by the General Formula (2) is aminomethanesulfonic acid or monoaminoethyl sulfate.

3. The structure according to claim 1, wherein the compound represented by the General Formula (1) is a compound represented by General Formula (3) below

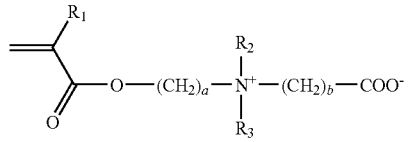

(3)

(in this formula, $R_1$ is a hydrogen atom or a methyl group; $R_2$, $R_3$ are independently selected from a methyl group, an ethyl group, an n-propyl group, and an iso-propyl group; a is an integer from 1 to 5; b is an integer from 1 to 4).

4. The structure according to claim 1, wherein the compound described by the General Formula (1) is a compound described by the following Chemical Formula (A), and the compound described by the General Formula (2) is selected from the group consisting of aminomethanesulfonic acid, and monoaminoethyl sulfate

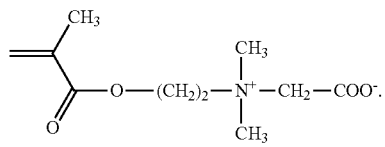

(A)

5. A target substance detection element having a substrate having a detection region, polymers present on a surface of the substrate, and first target substance capturing molecules bonded to the polymers, wherein each of the polymers comprises a polymer of a carboxybetaine monomer represented by General Formula (1) below;

the first target substance capturing molecules are bonded to some of the carboxyl groups of the polymers; and a compound represented by General Formula (2) is bonded to at least some of the carboxyl groups, from among the carboxyl groups of the polymers, that are not bonded to the first target substance capturing molecules

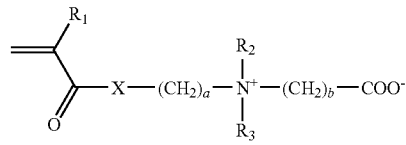

(1)

(in this formula, $R_1$ is a hydrogen atom or a methyl group; $R_2$ and $R_3$ are independently selected from a methyl group, an ethyl group, an n-propyl group, and an iso-propyl group; X is an oxygen atom or NH; a is an integer from 1 to 5; b is an integer from 1 to 4),

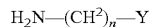

(2)

(in this formula, n is an integer from 1 to 4, such that n +b is an integer from 2 to 5; Y is $OSO_3H$ or $—SO_3H$).

6. A target substance detection kit comprising:

the target substance detection element according to claim 5; and a labeling material comprising a labeling substance and a second target substance capturing molecule.

7. The target substance detection kit according to claim 6, wherein the detection region is a region that can detect a magnetic substance; and the labeling substance is a magnetic substance.

8. The target substance detection kit according to claim 6, wherein the target substance detection element is an electrode; and the labeling substance is an enzyme.

9. The target substance detection kit according to claim 6, wherein the target substance detection element is a microtiter plate; and the labeling substance is selected from the group consisting of a gold colloid, latex bead, luminol, ruthenium, enzyme, a radioactive substance, and a fluorescent substance.

10. A method of using the structure according to claim 1, comprising bringing an analyte containing a target substance into contact with the structure, and detecting the target substance.

11. The structure according to claim 1, wherein the compound represented by the General Formula (2) is aminomethanesulfonic acid.

12. The target substance detection element according to claim 5, wherein the compound represented by the General Formula (2) is aminomethanesulfonic acid.

* * * * *